(12) United States Patent
Tanaka

(10) Patent No.: US 9,848,839 B2
(45) Date of Patent: Dec. 26, 2017

(54) RADIOGRAPHIC DEVICE

(71) Applicant: SHIMADZU CORPORATION, Kyoto-shi Kyoto (JP)

(72) Inventor: Masahiro Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 139 days.

(21) Appl. No.: 14/760,152

(22) PCT Filed: Dec. 18, 2013

(86) PCT No.: PCT/JP2013/083895
§ 371 (c)(1),
(2) Date: Jul. 9, 2015

(87) PCT Pub. No.: WO2014/119164
PCT Pub. Date: Aug. 7, 2014

(65) Prior Publication Data
US 2015/0351708 A1    Dec. 10, 2015

(30) Foreign Application Priority Data

Jan. 31, 2013 (JP) .............................. 2013-016639

(51) Int. Cl.
*A61B 6/04* (2006.01)
*A61B 6/10* (2006.01)
*A61B 6/00* (2006.01)

(52) U.S. Cl.
CPC .......... *A61B 6/0457* (2013.01); *A61B 6/0442* (2013.01); *A61B 6/10* (2013.01);
(Continued)

(58) Field of Classification Search
CPC ....... A61B 6/0457; A61B 6/548; A61B 6/032; A61B 6/04; A61B 6/0478; A61B 5/0555;
(Continued)

(56) References Cited

U.S. PATENT DOCUMENTS 6,094,760 A * 8/2000 Nonaka ................ A61B 6/0457
5/600
7,942,812 B2 * 5/2011 Sato ....................... A61B 1/042
600/101
(Continued)

FOREIGN PATENT DOCUMENTS

| JP | 2005-245636 | 9/2005 |
| JP | 2012-32204 | 2/2012 |
| WO | WO 2012/005303 | 1/2012 |

OTHER PUBLICATIONS

PCT/JP2013/083895, International Search Report dated Mar. 11, 2014, 1 pags—Japanese, 1 page—English.

*Primary Examiner* — Irakli Kiknadze
(74) *Attorney, Agent, or Firm* — Andrew F. Young, Esq.; Lackenbach Siegel, LLP

(57) ABSTRACT

An diagnostic X-ray radiography device and system whereby a subject (M) can be placed on and taken off of an imaging bed safely, easily, and comfortably. In the device and system a placement-accommodating-state memory (21) stores a plurality of placement-accommodating states each consisting of an imaging bed (1) position and orientation and an X-ray tube (4) position that accommodate a given placement state of the subject (M). A placement-accommodating-state control unit (22) is provided that, if a desired placement-accommodating state is specified from among the plurality of placement-accommodating states by means of a control panel (11), makes the position of the imaging bed (1) and the position of the X-ray tube (4) conform to the specified placement-accommodating state. A placement-accommodating state is thus set automatically, so that the subject (M) can be placed and removed from the imaging bed (1) easily without a collimator (4a) attached to the X-ray tube (4) getting in the way.

4 Claims, 10 Drawing Sheets

(52) U.S. Cl.
CPC ............ *A61B 6/102* (2013.01); *A61B 6/4435* (2013.01); *A61B 6/4452* (2013.01); *A61B 6/487* (2013.01); *A61B 6/589* (2013.01); *A61B 6/467* (2013.01)

(58) Field of Classification Search
CPC ..... A61B 6/0421; A61B 6/105; A61B 6/4014; A61B 6/4266; A61B 6/4458; A61B 6/4464; A61B 6/547; A61B 2090/376; A61B 2503/40; A61B 5/704; A61B 6/037; A61B 6/0442; A61B 6/10; A61B 6/102; A61B 6/4435; A61B 6/4452; A61B 6/467; A61B 6/487; A61B 6/589; H01M 10/0525; H01M 2/1626; H01M 4/0404; H01M 4/13; H01M 4/134; H01M 4/139; H01M 4/366; H01M 4/38; H01M 4/405; H01M 4/62; H01M 4/08; H01M 4/1395; H01M 4/03; Y02E 60/122; Y02P 70/54
USPC ............... 378/17, 20, 68, 69, 208, 209, 193; 5/601, 608, 600, 610
See application file for complete search history.

(56) References Cited

U.S. PATENT DOCUMENTS

2005/0228255 A1* 10/2005 Saracen ............... A61B 6/0457
600/407
2005/0234327 A1* 10/2005 Saracen ............... A61B 6/0457
600/407

* cited by examiner

RADIOGRAPHIC DEVICE

CROSS REFERENCE TO RELATED APPLICATION

This application references and claims priority as a national stage from PCT/JP2013/083895 filed Dec. 18, 2013 which in turn claims priority from JP 2013-016639 filed Jan. 1, 2013, the entire contents of each of which are incorporated herein by reference.

FIGURE SELECTED FOR PUBLICATION

FIG. 1.

BACKGROUND OF THE INVENTION

Field of the Invention

The present invention relates to for example, a medical X-ray diagnosis device to take X-ray radiography of the subject laid on the table, and further specifically relates to a technology to easily load the subject on the table and easily unload the subject from the table.

Description of the Related Art

Referring now to FIGS. 10A and 10B, a schematic view of the basic composition of the fluoroscopic table side of the conventional X-ray fluoroscopic system. As illustrated in FIG. 10A, the conventional fluoroscopic system comprises; the table 51 that can change the position and the posture thereof, when the subject (patient) M is loaded, the X-ray tube 53 and the X-ray detector 54 are facing each other, wherein the table 51 is in-between, and the X-ray radiographic mechanism 52 that moves the X-ray tube 53 and the X-ray detector 54 in the fluoroscopic table side, while keep facing each other in the longitudinal direction of the table 51. Then, referring to FIG. 10B, the X-ray fluoroscopic system lets the table 51 up and down by changing the position-and-posture of the table 51, and while the transmitted X-ray image of the subject M due to the X-ray irradiated to the subject M from the X-ray tube 53 is detected by the X-ray detector 54 and output to the latter step as the X-ray detection data, the X-ray fluoroscopic image is generated and displayed based on the X-ray detection data output from the X-ray detector 54.

One of such X-ray fluoroscopic systems is further constituted to control the table driving means and the X-ray radiographic system move means to coincide the suitable state storage module to store the position of the table 51 and the X-ray radiographic mechanism 52, which is suitable to ease loading and unloading the subject M, and the position-and-posture state of the table 51 and the position of the X-ray radiographic mechanism 52 with the suitable state for loading and unloading stored in the suitable stage storage means for loading and unloading (e.g., referring to Patent Document 1). It is deemed preferable that the suitable state for loading and unloading is the state in which the table 51 is horizontal and in the low position, and the X-ray radiographic mechanism 52 positions at either end position of the table.

Patent Document 1: JP Patent Published 2002-209885, the entire content of which is incorporated herein by reference.

ASPECTS AND SUMMARY OF THE INVENTION

Problems to be Solved by the Invention

However, in the case of loading the subject on the table 51 or unloading from the table 51, the move of the X-ray radiographic mechanism 52 takes a fair amount of time when the X-ray radiographic mechanism 52 is moved to the end of the table 51 and it is problematic that the dead-time until beginning of the examination is longer.

On the other hand, if a state in which only the table 51 is moved to the low position while holding the X-ray radiographic mechanism 52 near the center is stored as the suitable state for loading and unloading, the suitable state for loading and unloading can be obtained promptly, but it is problematic in many cases of that once the subject M sits on the table 51 in the state in which the subject M pushes out legs out of the table 51 and then lies face up on the table 51, and when the subject M is unloaded, the head would contact to the X-ray tube 53 in many cases of which the subject M takes a sitting posture on the table 51.

The purpose of the present invention is to provide a medical X-ray diagnostic device by which a subject can be safely loaded on and unloaded from a table so that the above problem can be solved.

Means for Solving the Problem

For solving the above problem, a medical X-ray diagnostic device comprises; a table on which a subject is loaded, a table driving means to change the position-and-posture state by changing at least one of the position of the table or the posture thereof, an X-ray radiographic means including the X-ray radiation means and the X-ray detection means facing each other and sandwiching the table, which is installed to the table or in the proximity thereof, a driving means for the X-ray radiation means to change the position in the perpendicular direction to the table plan of the X-ray radiation means, and further comprises; a suitable state for loading and unloading storage means to store the position-and-posture state of the table suitable for loading and unloading the subject and the position of the X-ray radiation means, a suitable state for loading and unloading control means to control said table driving means and the driving means for the X-ray radiation means as the position-and-posture state of the table and the position of the X-ray radiation means coincide with the suitable state for loading and unloading stored in the loading and unloading state storage means, and an input means to input the direction to the suitable state for loading and unloading control means.

Further, the X-ray radiographic system move means to change the position of the X-ray radiographic means along the longitudinal direction of the table may be included, and the suitable state for loading and unloading storage means also stores the position of the X-ray radiographic means suitable for loading and unloading of the subject, and the suitable state for loading and unloading control means may control the X-ray radiographic system move means as letting coincide also the position of the X-ray radiographic means with the suitable state for loading and unloading.

Further, according to either above inventions, the suitable state for loading and unloading control means controls the table driving means and the X-ray radiation means by which both the table and the X-ray radiation means are operative while the direction is being given by the input means, and also then after; in the case of no direction given by the input means, ceases an operation other than by the driving means for the X-ray radiation means; and also controls the X-ray radiation means as it may be continuously operative. Further, it is preferable that only when the table is in the horizontal state, the continuous operation can be operative.

Effects of the Invention (Action) The inventor sets forth the action of the medical X-ray diagnostic device of the present invention. According to the medical X-ray diagnostic device of the present invention, when the subject is loaded on or unloaded from the table, the suitable state for loading and unloading control means controls the table driving means and the driving means for the X-ray radiation means once the operator operates the input means so that at least either one of the position of the table or the posture thereof may change and the position-and-posture state of the table and the position of the X-ray radiation means coincide with the suitable state for loading and unloading stored in the suitable state for loading and unloading state storage mean.

Specifically, according to the medical X-ray diagnostic device of the present invention, not only the position-and-posture state of the table but also the position of the X-ray radiation means are in the suitable state for loading and unloading, particularly the X-ray radiation means has moved to the suitable position, so that the incident as an interference between the subject M and the X-ray radiation means can be avoided. Accordingly, the subject can be safely loaded on and unloaded from the table. Particularly, the object to be moved is extremely small compared to the X-ray radiographic means so that the speedy action can be expected.

Further, when the X-ray radiographic means per se is moved, the incident of the interference between the subject and the X-ray radiation means can be further adequately avoided so that the subject can be safely loaded on and unloaded from the table.

Further, if the X-ray radiation means is continuously operated despite no direction from the input means thereafter, the operator can unlink hands to the switch and can help to load and unload the subject while the X-ray radiation means is retreating so that even fewer personnel can quickly conduct the examination. In addition, ceasing the operation of other than the X-ray radiation means is conducted under consideration of safety and the operation to move the X-ray radiation means in the retreating direction (direction away from the table) is the move toward the safer direction so that no concern as for safety takes place despite the continuous operation under unlinking hands to the switch. Particularly, if the continuous operation under unlinking hands to the switch is limited to the case in which the table is in the horizontal state, the X-ray radiation means moves toward the ceiling and there is no fear to collide with the other obstacle at all so that it is desirable.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
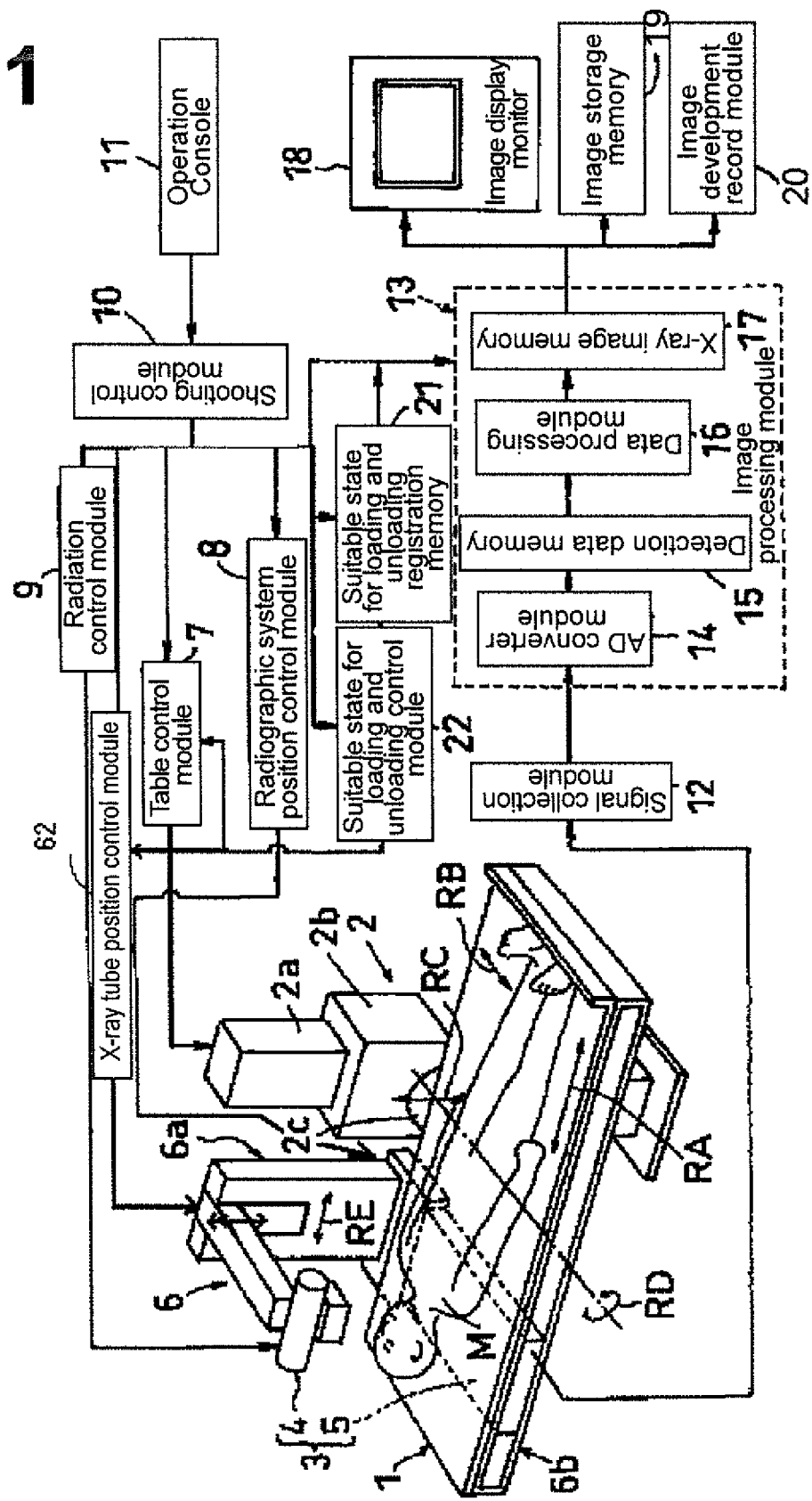
FIG. 1 is a block diagram illustrating the total system of the X-ray fluoroscopic device of Embodiment.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Referring to FIG. 1, an X-ray fluoroscopic device of one Embodiment of the medical X-ray diagnostic device of the present invention is provided. FIG. 1 is a block diagram illustrating the total system of the X-ray fluoroscopic device relative to Embodiment.

Figure 2:
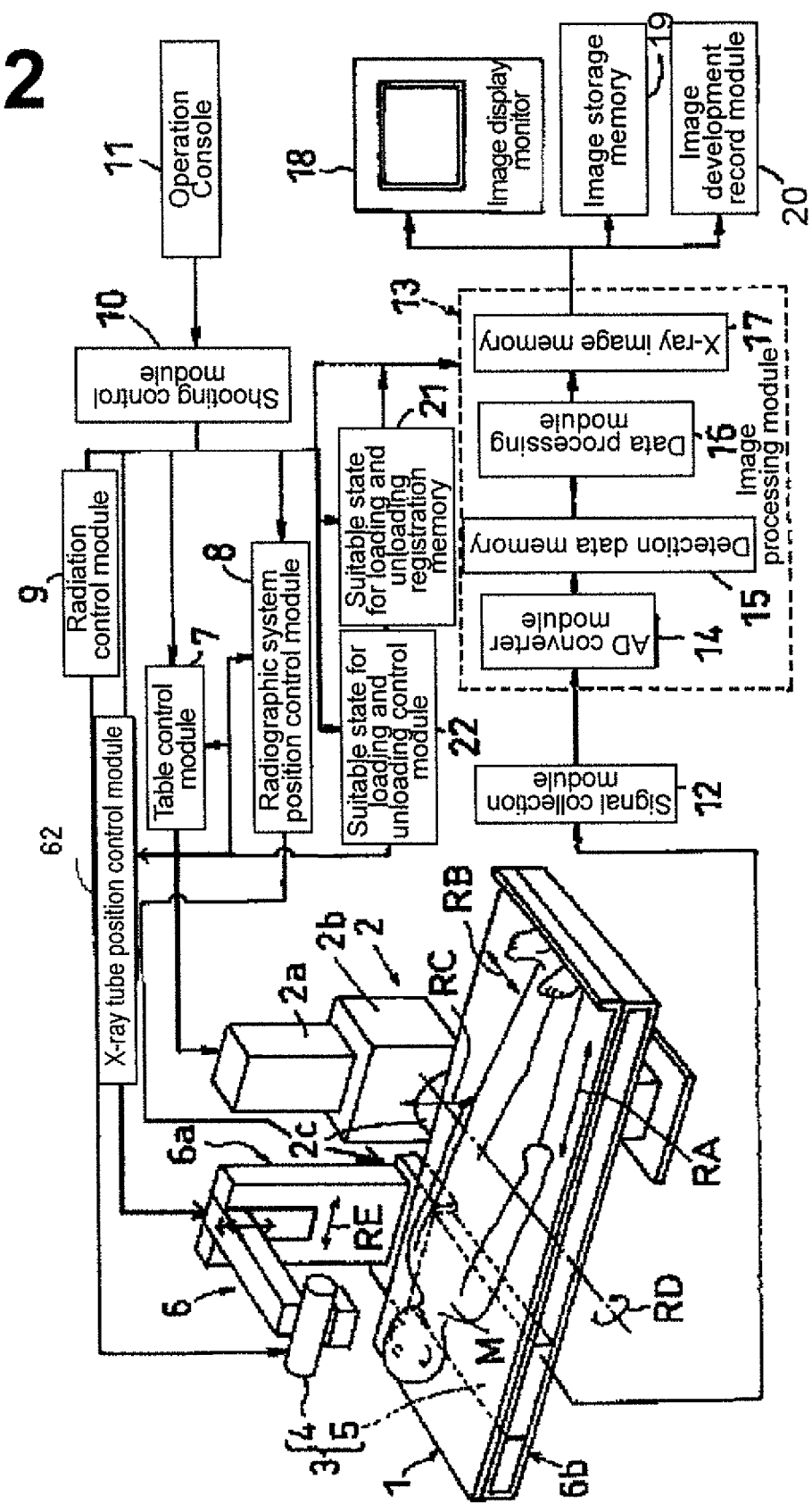
FIG. 2 is a block diagram illustrating the total system of the X-ray fluoroscopic device of another Embodiment.

Referring to FIG. 2, an X-ray fluoroscopic device of another Embodiment of the medical X-ray diagnostic device of the present invention is provided. FIG. 2 is a block diagram illustrating the total system of the X-ray fluoroscopic device relative to another Embodiment.

Referring to FIG. 1, the X-ray fluoroscopic device includes; the table 1 on which the subject M is loaded, the table driving module 2 to change the position-and-posture state of the table 1 by changing the position and the posture of the table 1, and the X-ray radiographic mechanism 3 having the X-ray tube 4 and the X-ray detector 5 is set on the table 1 in the fluoroscopic side, which are facing and sandwiching the table 1. Then, the X-ray fluoroscopic system lets the table 1 up and down by changing the position-and-posture of the table 1, and while the transmitted X-ray image of the subject M due to the X-ray irradiated to the subject M from the X-ray tube 4 is detected by the X-ray detector 5 and output to the latter step as the X-ray detection data, the X-ray fluoroscopic image is generated and displayed constitutionally based on the X-ray detection data output from the X-ray detector 5. Hereafter, the inventor specifically sets forth each component of the X-ray fluoroscopic device of Embodiment.

The device of the present Embodiment constitutes e.g., the position-and-posture state of the table 1, which is changed by changing the position and the posture of the table 1. Specifically, the table driving module 2 is operative in that; the table 1 is movable reciprocally and linearly in the longitudinal (back and forth) direction of the table 1 as indicated by the arrow RA; movable reciprocally and linearly in the width (right and left) direction of the table 1 as indicated by the arrow RB, movable reciprocally and linearly in the perpendicular (up and down) direction of the table 1 as indicated by the arrow RC and also the entire table 1 is movable reciprocally and linearly as indicated by the arrow RD. Specifically, referring to FIG. 3, a combination of move of the table 1 is conducted, as indicated by the arrows RA-RD, and the constitution thereof let the table 1 such as up and down by changing the position and the posture of the table 1. Specifically, the move indicated by the arrow RA-RD is a factor to change the position-and-posture of the table 1. Further, a mechanism that conducts moves indicated by the arrow RA-RD as described above is feasible with the move mechanism using a rack and a pinion or the move mechanism using a ball screw, and so forth.

Figure 3:
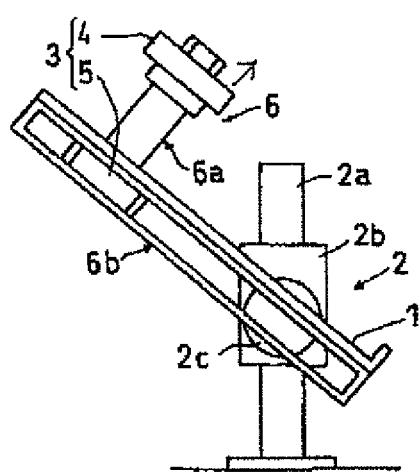
FIG. 3 is a schematic front view illustrating the state in letting the table up and down relative to the X-ray fluoroscopic device of Embodiment.

Further specifically, referring to FIG. 1 and FIG. 3, the up-and-down block 2b that allows the supporting pole 2a installed perpendicular on the floor to go up and down in the up-and-down direction (direction of arrow RC) is installed in the table driving module 2. The revolving arm 2c revolvable around the axis that is extending in the width direction (direction of arrow RB) of the table 1 and the mechanism (not shown in FIG.) to move linearly the table 1 back and forth (direction of arrow RA) and right and left (direction of arrow RB) are installed to the up-and-down block 2b. The lower side of the table 1 is supported by the revolving arm 2c. Accordingly, the table driving module 2 constitutes the move of the table 1 indicated by the arrow RA-RD by the up-and-down movement of the up-and-down block 2b, the revolving movement of the revolving arm 2c and the linear movement by the back-and-forth/right-and-left linear move mechanism. In addition, control of the table driving module 2 to move the table 1 in accordance with the arrow RA-RD is conducted by the table control module 7.

On the other hand, the X-ray radiographic mechanism 3 installed on the table 1 constitutes the move is not only integrally with the table 1 along with the move of the table 1 indicated by the arrow RA-RD, but also the back-and-forth linear move in the longitudinal direction of the table 1 by the X-ray radiographic system move module 6 as indicated by the arrow RE, and changing the position of the X-ray radiographic mechanism 3 in the longitudinal direction of the table 1. Specifically, the move indicated by the arrow RE is a factor to change the position of the X-ray radiographic mechanism 3. Specifically, referring to FIG. 4, the X-ray radiographic mechanism 3 constitutes being changeable between the front end position shown as the solid line and the rear end position shown as the dotted line by the X-ray radiographic system move module 6. Further, a mechanism that conducts linear move indicated by the arrow RE as described above is also feasible with the move mechanism using a rack and a pinion or the move mechanism using a ball screw, and so forth.

Figure 4:
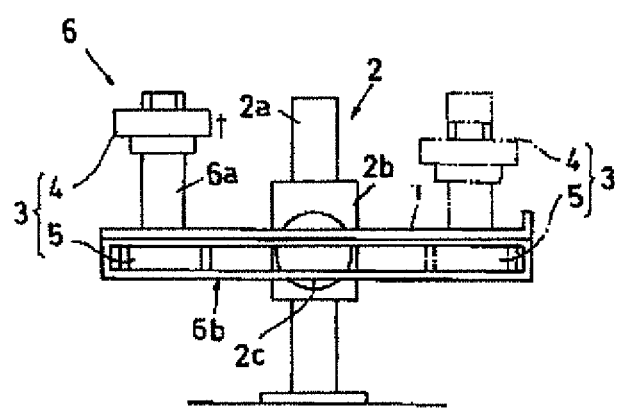
FIG. 4 is a schematic front view illustrating the state of the position change of the X-ray radiographic mechanism relative to the X-ray fluoroscopic device of Embodiment.

As further specifically set forth referring to FIG. 1 and FIG. 4, the X-ray radiographic system move module 6 comprises the support pole 6a having a U-like shape, on which the X-ray tube 4 and the X-ray detector 5 are installed and facing, and the frame-like plate 6b that is installed on the underside of the table 1 and of which both side faces are open, wherein the support pole 6a under the condition in which the X-ray detector 5 is enclosed inside the frame-like plate 6b moves linearly in the longitudinal (back-and-forth) direction of the table 1 and then the position of the X-ray radiographic mechanism 3 changes in the longitudinal direction of the table 1. In addition, control of the X-ray radiographic system move module 6 that conducts the move of X-ray radiographic mechanism 3 in accordance with the arrow RE is conducted by the radiographic system position control module 8.

On the other hand, the X-ray tube 4 includes the collimator 4a in the front side thereof to specify the range of X-ray radiation. According to the device of Embodiment, the X-ray tube 4 is installed as movable in the up-and-down direction (perpendicular direction to the surface of the table and the away direction from the table is the up direction and the close direction to the table is the down direction) relative to the U-like shape support pole 6a and the X-ray move module 61 to control the position of the X-ray tube by a motor and the X-ray tube position control module 62 to control therefor are installed. By ordinary, the distance between the X-ray detector 5 and the X-ray tube (SID) is controlled and managed by the X-ray tube position control module 62. Here, the X-ray tube move module 61 (or the control system including the X-ray tube position control module) corresponds to the driving means of the X-ray radiation means of the present invention.

On the other hand, the X-ray detector 5 is so called a flat panel type X-ray detector (FPD) in which many X-ray detection elements are arrayed lengthwise and breadthwise is thinner and lighter than the |•| tube. According to the device of Embodiment, the constitution of the X-ray detector 5 is operative to be able to cover the shortage of the X-ray detection area by the subtle move in the longitudinal direction of the table 1.

When the X-ray fluoroscopy is conducted, the X-ray tube 4 constitutes the radiation in accordance with the setup radiation condition of the tube voltage and the tube current and so forth by control of the radiation control module 9 including a high voltage generator and so forth. Further, controls by the above X-ray tube position control module 62, the table control module 7 and the radiographic system position control module 8 or the radiation control module 9 are conducted in accordance with signals transmitted from the shooting control module 10 along with the input operation through the operation console 11 and so forth.

Further, the signal collection module 12 to collect the X-ray detection data and then output the signals to the image processing module 13 is installed on the latter part of the X-ray detector. Further, the image processing module 13 comprises the AD converter module 14 that converts the X-ray detection data to the digital signals, the detection data memory 15 that stores the digitized X-ray detection data, the data processing module 16 that generates the X-ray image by conducting necessary image processing, e.g., edge-enhancing or filtering and so forth as for the X-ray detection data stored in the detection data memory 15, and the X-ray image memory 17 that stores the X-ray fluoroscopic image obtained by the image processing. Normally, in the case of X-ray fluoroscopy, the X-ray images stored in the X-ray image memory 17 are continuously renewed.

Further, the X-ray fluoroscopic device of Embodiment also comprises the image display monitor 18 that displays the X-ray fluoroscopic image stored in the X-ray image memory 17, the image development recording module 19 that develops the X-ray fluoroscopic image stored in the X-ray image memory 17 on a sheet such as a film and outputs as the X-ray photograph according to the direction from the operation console 11 or by an input operation while conducting X-ray fluoroscopy, and also the image storage memory 20 that records and stores the X-ray fluoroscopic images.

And further, the X-ray fluoroscopic device of Embodiment also comprises, as constitutionally remarkable and characteristic aspect, the suitable state for loading and unloading storage memory 21 that stores the position and the posture of the table 1 suitable (the position-and-posture state of the table 1) for the subject M to be loaded and unloaded and the position of the X-ray tube 4 as a suitable state for loading and unloading, and the suitable state for loading and unloading control module 22 that controls the table driving module 2 and the X-ray tube move module 61 to coincide the position and the posture of the table 1 (the position-and-posture state of the table 1) and the position of the X-ray tube 4 with the suitable state for loading and unloading stored in the suitable state for loading and unloading storing memory 21.

Here, according to the above Embodiment, for the purpose of speedy move, the suitable state for loading and unloading control module 22 does not control the position of the X-ray radiographic mechanism 3 but controls the position and the posture of the table 1 suitable (the position-and-posture state of the table 1) for the subject M to be loaded and unloaded and the position of the X-ray tube 4. However, if easiness or safety for loading and unloading is prioritized rather than speedy move therefor, it is desirable that the suitable state for loading and unloading control module 22 also controls the X-ray radiographic system move module 6 to store also the position of the X-ray radiographic mechanism 3 suitable for the subject M to be loaded and unloaded also in the suitable state for loading and unloading storing memory 21 and, referring to FIG. 2, coincide it with the suitable state for loading and unloading stored in the suitable state for loading and unloading storage memory 21. Hereafter, referring to FIG. 2, the inventor further more specifically sets forth the suitable state for loading and unloading storing memory 21 and the suitable state for loading and unloading control module 22.

Referring to FIG. 2, the suitable state for loading and unloading storing memory 21 of Embodiment stores a plurality of the suitable states for loading and unloading and also is constitutionally operable to specify the specific suitable state for loading and unloading among a plurality of the suitable states for loading and unloading stored in the suitable state for loading and unloading storing memory 21 through the operation console 11.

In other words, if the subject M is healthy adult, even if the state of the table 1 or the X-ray radiographic mechanism 3 is more or less uncomfortable for loading and unloading, it may not be so inconvenient, but if the subject M is particularly a person in need of nursing care such as an elder or the injured or a small child, the state of the table 1 and the X-ray radiographic mechanism should be the suitable state for loading and unloading that is comfortable for loading and unloading. In other words, normally, the suitable state for loading and unloading is not only one but a variety of suitable states for loading and unloading can exist in accordance with the condition of the subject M.

Figure 5:
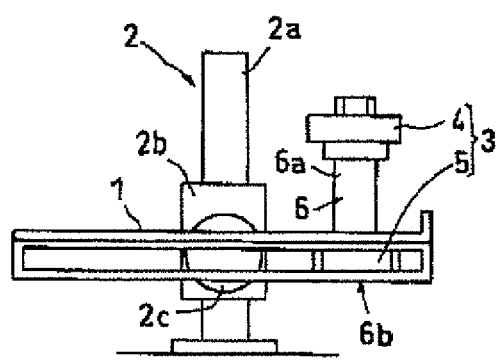
FIG. 5 is a schematic front view illustrating the setting situation of one Embodiment in the suitable state for loading and unloading relative to the X-ray fluoroscopic device of Embodiment.

If the subject M is, e.g., a small child or a foot-injured, for example, referring to FIG. 5, the suitable state for loading and unloading is the state, wherein the table 1 is in place horizontal and in a lower position, the X-ray tube 4 is in place in the farthest away from the table 1, and the X-ray radiographic mechanism 3 is in place closer to the rear end (foot side) (hereafter, the suitable state for loading and unloading A). If the suitable state for loading and unloading A is set up, the small child or the foot-injured can sit near the center side of the table 1 (near the center between the front end of the table 1 (head side) and the rear end of the table 1 (foot side) and then get on the table 1 so that the small child or the foot-injured can be gotten on the table 1 and down therefrom without being disturbed by the X-ray radiographic mechanism 3.

Figure 6:
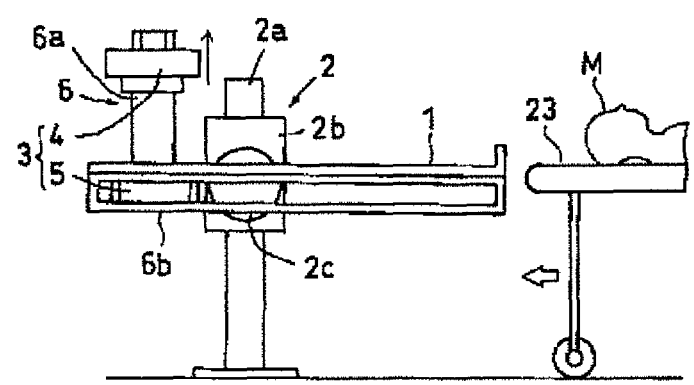
FIG. 6 is a schematic front view illustrating the setting situation of another Embodiment in the suitable state for loading and unloading relative to the X-ray fluoroscopic device of Embodiment.

If the subject M is, e.g., a bedridden person in need of nursing care, for example, referring to FIG. 6, the suitable state for loading and unloading is the state in which the table 1 is horizontal in place, the height of the table 1 is the same height of the mobile platform 23 such as the subject carrier stretcher set alongside the table 1 in place, the X-ray tube 4 is set in the farthest away position from the table and the X-ray radiographic mechanism 3 is set close to the front end of the table 1 (head side) in place (the suitable state for loading and unloading B). In the case of the suitable state for loading and unloading B, for example, the mobile platform 23 is set next to the side of the table 1 therealongside and even the person in need of nursing care can be assisted by a plurality of people from both sides of table 1 (side of both sides) without being disturbed by the X-ray radiographic mechanism 3, and accordingly the subject M on the mobile platform 23 can be easily loaded on the table 1 and reversely the subject M on the table 1 can be unloaded easily to the mobile platform 23.

Further, if the subject M is a healthy person, the suitable state for loading and unloading is the state in which the table 1 stands perpendicular posture and the X-ray radiographic mechanism 3 is in the front side (head side) in place (the suitable state for loading and unloading C). In the case of the suitable state for loading and unloading C, the subject M can be easily loaded and unloaded without being disturbed by the X-ray radiographic mechanism 3.

However, since moving of the X-ray radiographic mechanism 3 requires reasonable time, it is desirable that the X-ray radiographic mechanism 3 should not be moved if the speedy examination is expected. However, in that case, if there is the X-ray radiographic mechanism 3 near the center, the head may contact the collimator installed in the X-ray tube 4 because of sitting and getting on the table 1. If the X-ray tube 4 would be moved upward to avoid that, the risk as the head contacts could be reduced. Further, even in the upright position, it is desirable that the X-ray tube is moved away from the table 1 so that the subject M can stay away from contacting the collimator 4a as much as possible.

Needless to say, the suitable state for loading and unloading set up by the suitable state for loading and unloading control module 22 is not limited to the above suitable state for loading and unloading A-C and a suitable state for loading and unloading other than the suitable state for loading and unloading A-C can be stored and the state thereof can be set up. Based on the above reasons, in any case, it seems that the position where the X-ray tube 4 is the farthest away from the table 1 is the suitable state for loading and unloading. However, if the subject M is a small child, the head thereof might not physically contact even without moving the X-ray tube to the position farthest away from the table 1 and in the case of upright position, the X-ray tube 4 might not be moved to the farthest away position from the table 1 due to the positional relationship with other obstacle and so forth. Accordingly, the suitable state for loading and unloading is not limited to the farthest away position from the table 1 and can be set arbitrarily. Further, the suitable state for loading and unloading other than suitable state for loading and unloading A-C may be, e.g., the suitable state for loading and unloading in which the X-ray radiographic mechanism 3 is in the center so that care personnel can stand easily in both longitudinal sides of the table, the suitable state for loading and unloading in which the height of the table 1, in FIG. 6, is lower and other states than that are the same states is suitable for the subject in a wheelchair, and so forth, and a variety of states can be listed based on the combination of the height of the table 1 (position) and the posture (horizontal, upright and tilted posture and so forth) and the position of the X-ray radiographic mechanism 3.

Figure 7:
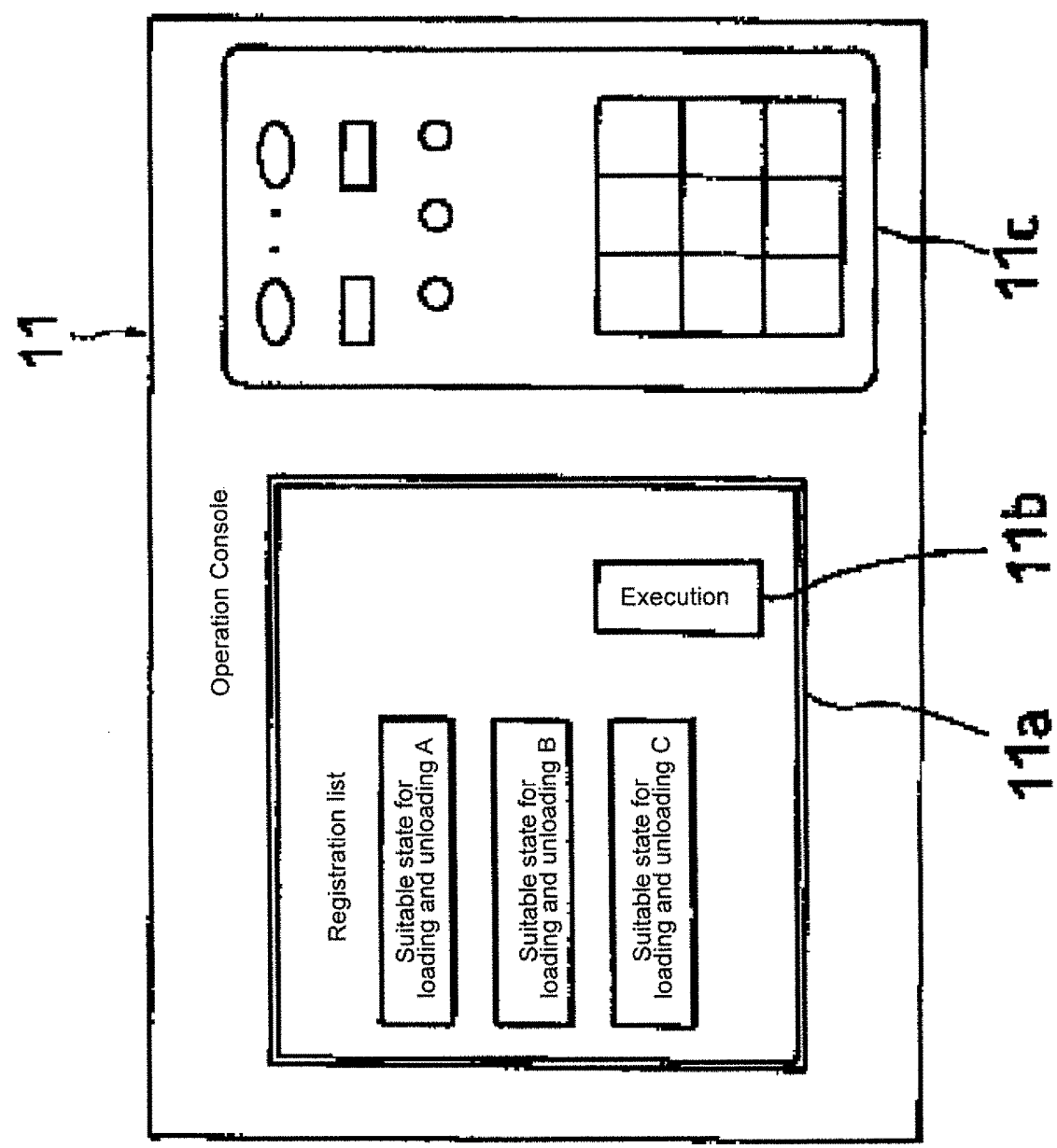
FIG. 7 is a diagram illustrating the console with the liquid crystal display for display/specification of the suitable state for loading and unloading relative to the X-ray fluoroscopic device of Embodiment.

Further, according to the device of Embodiment referring to FIG. 7, the suitable state and method for loading and unloading A-C stored in the suitable state for loading and unloading storage memory 21 is read out on the screen of the liquid crystal display 11a of the operation console 11 according to the input operation in the operation console 11 and the list of the suitable state for loading and unloading A-C is displayed, and then after an operator touches the specific one of the suitable state for loading and unloading A-C to input, if continuously the execution switch 11b is touched, the X-ray tube move module 61, the table driving module 2, and the X-ray radiographic system move module 6 are controlled by the suitable state for loading and unloading control module 22 through the X-ray tube position control module 62, the table control module 7 and the radiographic system position control module 8, and then the position and the posture of the table 1 and the position of the X-ray tube 4 and the X-ray radiographic mechanism 3 coincide with the above specified suitable state for loading and unloading and set up automatically as the above specified suitable state for loading and unloading. Needless to say, as described above, if a speedy examination is desirable, the position of the X-ray radiographic mechanism 3 may not be controlled. Further, 11c shown in FIG. 7 is an input panel having various kinds of input switches.

Figure 8:
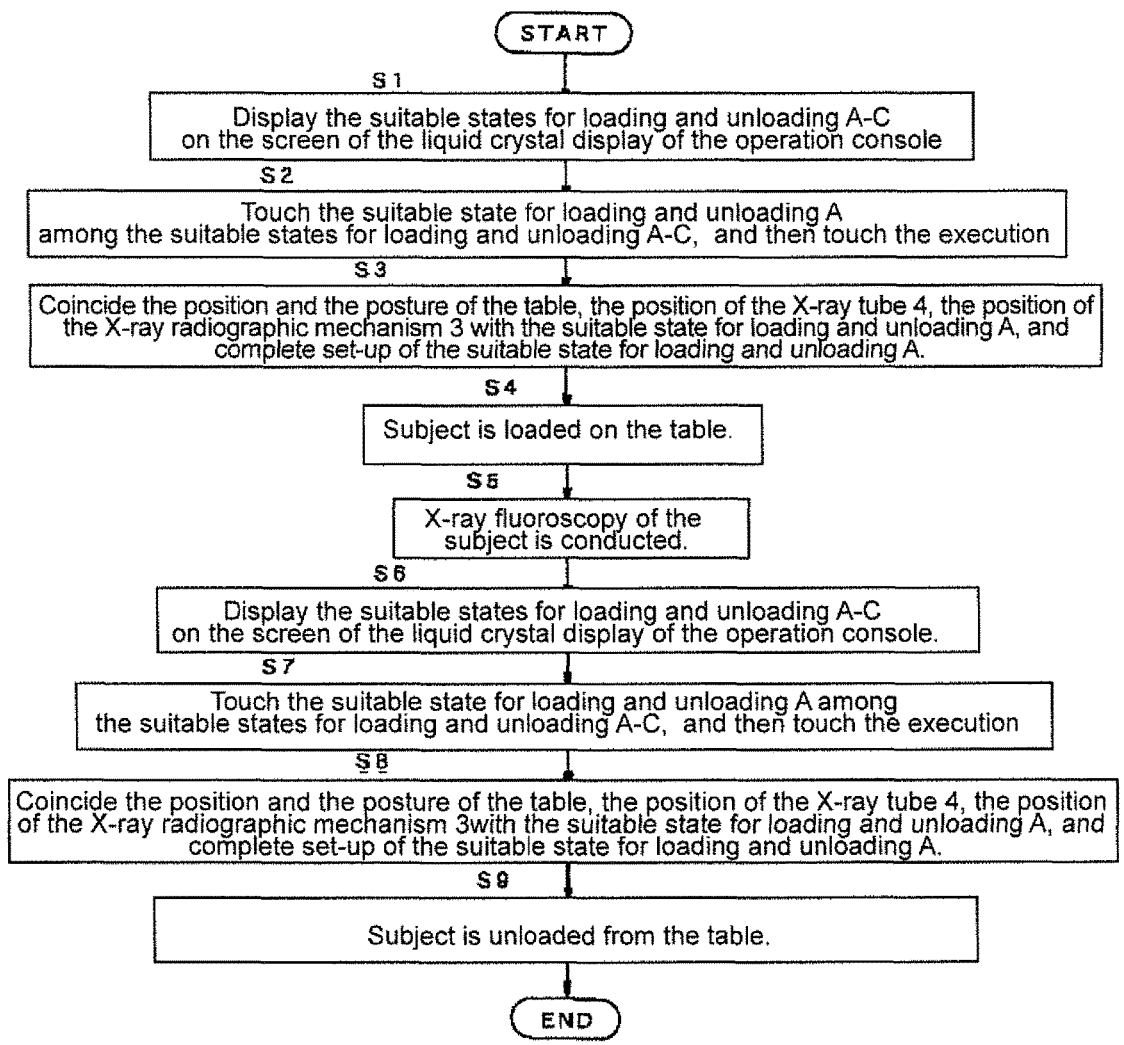
FIG. 8 is a flow diagram illustrating the ongoing process of the X-ray fluoroscopy by the X-ray fluoroscopic device of Embodiment.

Next, the inventor sets forth the ongoing process as for execution of the X-ray fluoroscopy according to the above device of Embodiment referring to FIGs and focusing on getting on and off from the table 1. FIG. 8 is a flow diagram illustrating the ongoing process of the X-ray fluoroscopy by the X-ray fluoroscopic device of Embodiment.

(Step 1) Firstly, referring to FIG. 7, the operator reads out the list of a plurality of suitable states for loading and unloading A-C stored in the suitable state for loading and unloading storage memory 21 and displays on the screen of the liquid crystal display 11a of the operation console 11.

(Step 2) The operator touches and specifies, e.g., the suitable state for loading and unloading A (touch screen input) from the suitable states for loading and unloading A-C, which match to the X-ray fluoroscopic target subject M (e.g., a small child), and then touches the execution switch 11b (touch screen input).

(Step 3) The suitable state for loading and unloading control module 22 becomes operative to coincide the position and the posture of the table 1, the position of the X-ray tube 4 and the position of the X-ray radiographic mechanism 3 with the suitable state for loading and unloading, and referring to FIG. 5, the suitable state for loading and unloading A is automatically set up.

(Step 4) The subject M is loaded on the table 1 that is set as the suitable state for loading and unloading A.

(Step 5) As needed, the position of the X-ray tube 4 and the X-ray radiographic mechanism 3 and the position of the table 1 are changed and the X-ray ray fluoroscopy of the loaded subject M is conducted.

(Step 6) Firstly, following the X-ray fluoroscopy, the operator reads out again the list of the suitable states for loading and unloading A-C and displays on the screen of the liquid crystal display 11a of the operation console 11.

(Step 7) The operator touches again the suitable state for loading and unloading A among the suitable states for loading and unloading A-C and then touches the execution switch.

(Step 8) The suitable state for loading and unloading control module 22 becomes operative also and referring to FIG. 5, the suitable state for loading and unloading A is automatically set up again.

(Step 9) Once the subject M is unloaded on the table 1 that is set as the suitable state for loading and unloading A, the X-ray fluoroscopy is completed.

As described in detail above, according to the X-ray fluoroscopic device of Embodiment, if an appropriate state among the suitable states for loading and unloading A-C stored in the suitable state for loading and unloading storage memory 21 is touched and specified by the operation console 11, the suitable state for loading and unloading control module 22 becomes operative to coincide the position and the posture of the table 1, the position of the X-ray tube 4 and the position of the X-ray radiographic mechanism 3 with the suitable state for loading and unloading, and the suitable state for loading and unloading A is automatically set up so that the subject M can be easily loaded on the table 1 and unloaded therefrom and the X-ray fluoroscopy can be smoothly proceeded.

Here, from safety standpoints, the suitable state for loading and unloading control module may be only operative while the above execution switch is being pushed down and when the execution switch is released, it may cease. However, the move of the X-ray tube 4 which is in the away direction from the table 1 may not cause a problem as for safety so that the ongoing operation can be controlled even after no input from the execution switch. According to such control, the subject M can be taken care while the X-ray tube is moving so that even fewer can conduct a speedy examination. Further, in the case of upright position, even when the X-ray tube is moved in a direction away from the table 1, it is expected that there is an obstacle in front. Accordingly, only when the table is horizontal, the control may allow continuously operative after there is no longer input from the execution switch.

Further, when the position that is not the farthest position from the table is registered as the suitable state for loading and unloading of the X-ray tube 4 and the X-ray tube is located farther from the registration position, it is predicted that the X-ray tube may move in the direction close to the table when the execution switch is pushed. If this may cause a problem, it may be controlled as the X-ray tube 4 must be only operative in the direction away from the table 1.

The present invention is not limited to the above Embodiment and further another alternative Embodiment can be implemented.

Figure 9:
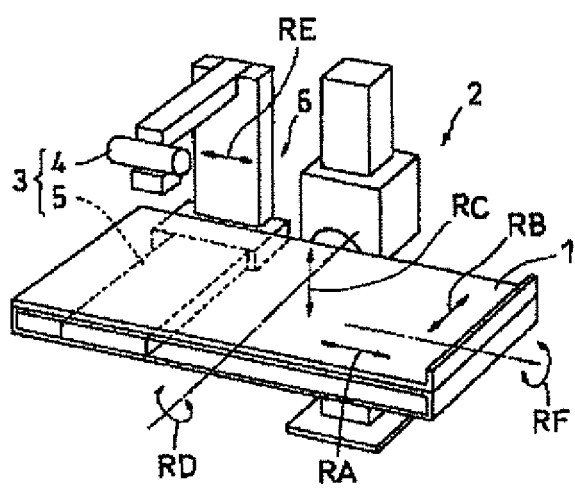
FIG. 9 is a schematic perspective view of the basic composition of the fluoroscopic table side of the X-ray fluoroscopic device of an alternative Embodiment.
Figure 10A:
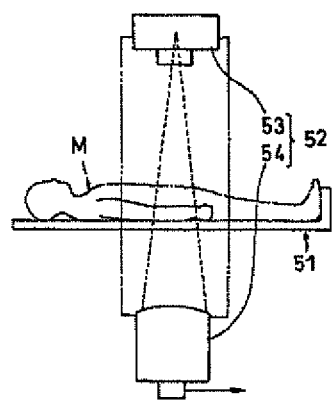
FIGS. 10A, 10B are schematic views of the conventional arrangement of a fluoroscopic table side of a conventional X-ray fluoroscopic device.
Figure 10B:
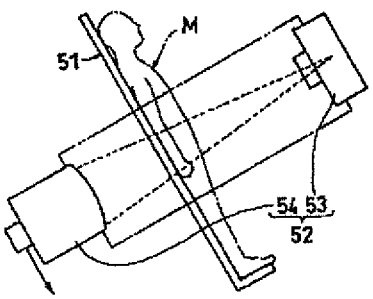

(1) Referring to FIG. 9, an alternative Embodiment to the above Embodiment may include the constitution, wherein the table 1 as the entire table 1 can move back-and-forth and revolve around the revolving axis in the longitudinal direction of the table 1 as indicated by the arrow RF in addition to the move by the table driving module 2 as indicated by the arrow RA-RD in order to change the position-and-posture of the table 1. In that case, the revolving position indicated by the arrow RF may be included in the revolving move by the table driving module 2 and, at the same time, may be included in the factor of the suitable state for loading and unloading.

(2) Further, according to the above device of Embodiment, the position-and-posture state of the table 1 is changed by changing the position of the table 1 and the posture thereof, but only either one of the position of the table 1 or the posture of the table 1 may be changed to change the position-and-posture state of the table 1 and then the position of the table 1 and the posture of the table 1 may be changed.

(3) Further, according to the above device of Embodiment, the table 1 has a step on which the subject puts feet, but the table 1 is not limited to such form and a variety of forms may be applied.

(4) Further, according to the above device of Embodiment, the X-ray detector 5 is a flat panel type X-ray detection sensor, but the X-ray detector 5 may include other detector such as I•I tube.

(5) Further, according to the constitution of the above device of Embodiment, one of a plurality of the stored suitable states for loading and unloading can be specified and selected, but as the constitution of the alternative Embodiment, the device having one stored suitable state for loading and unloading can be included.

(6) Further, according to the constitution of the above device of Embodiment, one of a plurality of the stored suitable states for loading and unloading can be specified and selected by an touch operation of the liquid crystal display 11a, but, for example, as the constitution of the alternative Embodiment, the device that can specify the suitable state for loading and unloading by clicking the mouse and the device having another specification method and so forth can be included.

(7) Further, according to the above device of Embodiment, the X-ray radiographic mechanism 3 is installed on the table 1, but, as the constitution of the alternative Embodiment, the device having the constitution in which the X-ray radiographic mechanism 3 is mounted on the radiographic system position move module installed alongside (in the side of) the table 1 differently from the table 1 and the X-ray radiographic mechanism 3 is not installed on the table 1 and the position of the X-ray radiographic mechanism 3 changes in the longitudinal direction of the table 1 can be included.

(8) Further, according to the constitution of the above device of Embodiment includes the image storage memory 19 or the image development record module 20, but, as the constitution of the device of the alternative Embodiment, the device having the constitution in which either or neither the image storage memory 19 or the image development record module 20 is included can be included.

(9) Further, according to the above device of Embodiment, the X-ray fluoroscopic device having the constitution in which the snap filming device to develop the transmitted X-ray image on the photo film is included together can be included in the alternative Embodiment.

(10) The medical X-ray diagnostic device is not limited to the X-ray fluoroscopic device of Embodiment and may include, e.g., an X-ray CT device.

(11) The stored suitable state for loading and unloading according to the X-ray fluoroscopic device of the present invention is not required to be plural and only a single suitable state for loading and unloading can be stored. In that case, the selection steps for the suitable state for loading and unloading can be excluded.

(12) The suitable state for loading and unloading according to the X-ray fluoroscopic device of the present invention can be stored along with the shooting condition, the shooting order, the operative procedure and other information. In that case, when other information is selected, the best suitable state for loading and unloading can be automatically set up.

In view of the above steps, discussions, and arrangements, it will also be understood that the present invention includes a system and a method for using such a device or system as well all within the scope and spirit of the present invention.

EXPLANATION OF REFERENCES

1 Table
2 Table driving module
3 X-ray radiographic mechanism (X-ray radiographic means)
4 X-ray tube (radiation source)
5 X-ray detector
6 X-ray radiographic system move module
11 Operation console (suitable state for loading and unloading specifying means and modules and systems)
21 Suitable state for loading and unloading control memory (registration means and modules or system for the suitable state for loading and unloading)
22 Suitable state for loading and unloading control module
M Subject Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:
1. An X-ray diagnostic device, comprising:
a table operative to receive an external subject for scanning;
a table driving system operative to change a position-and-posture state by changing at least one of a position of said table and a posture of said table during a use thereof;
an X-ray radiographic system including an X-ray radiation module and an X-ray detection module facing each other and operatively sandwiching said table and positioned on either proximate side thereof;
an X-ray radiation module driving system operative to position the X-ray radiation module along a perpendicular direction relative to a plane of said table;
a suitable state for loading and unloading memory module operative to store a position-and-posture state of said table being suitable for a loading and unloading said external subject and a position of said X-ray radiation module as a suitable state for loading and unloading in advance of said use;
a suitable state for loading and unloading control system operative to control said table driving module and said X-ray radiation module driving system as a position-and-posture state of said table and a position of said X-ray radiation module coinciding with a suitable state for loading and unloading stored in said loading and unloading state storage module;
an input module operative to input a direction to the suitable state for loading and unloading control module during said use;
an X-ray radiographic system moving system operative to change the position of said X-ray radiographic system along a longitudinal direction of the table;
wherein said suitable state for loading and unloading storage module also operatively stores the position of said X-ray radiographic system being suitable for loading and unloading said external subject;
said suitable state for loading and unloading control system operatively controlling said X-ray radiographic moving system as the position of said X-ray radiographic module also coincides with a suitable state for loading and unloading;
wherein said suitable loading and unloading control module controls said table driving module and said driving module for the X-ray radiation module operative so that both said table and said X-ray radiation modules are operative while a direction from said input module is ongoing, and
wherein, afterward when there is no ongoing direction from said input module, said device ceases operations other than said driving module for the X-ray radiation driving module and also operatively controls said X-ray radiation module for continuous operation thereof.

2. The X-ray diagnostic device, according to claim 1, wherein:
said continuous operation is only operative when the table is in a horizontal state.

3. An X-ray diagnostic device, comprising:
a table operative to receive an external subject for scanning;
a table driving system operative to change a position-and-posture state by changing at least one of a position of said table and a posture of said table during a use thereof;
an X-ray radiographic system including an X-ray radiation module and an X-ray detection module facing each other and operatively sandwiching said table and positioned on either proximate side thereof;
an X-ray radiation module driving system operative to position the X-ray radiation module along a perpendicular direction relative to a plane of said table;
a suitable state for loading and unloading memory module operative to store a position-and-posture state of said table being suitable for loading and unloading said external subject and a position of said X-ray radiation module as a suitable state for loading and unloading in advance of said use;
a suitable state for loading and unloading control system operative to control said table driving system and said X-ray radiation module driving system as a position-and-posture state of said table and a position of said X-ray radiation module coinciding with the suitable state for loading and unloading stored in said loading and unloading state storage module;
an input module operative to input a direction to the suitable state for loading and unloading control module during said use;
wherein said suitable loading and unloading control module controls said table driving module and said driving module for the X-ray radiation module operative so that both said table and said X-ray radiation modules are operative while a direction from said input module is ongoing, and
wherein, afterward when there is no ongoing direction from said input module, said device ceases operations other than said X-ray radiation module driving system and also operatively controls said X-ray radiation module for continuous operation thereof.

4. The X-ray diagnostic device, according to claim 3, wherein:
said continuous operation is only operative when the table is in a horizontal state.

* * * * *